United States Patent [19]

Eyer

[11] Patent Number: 5,084,578
[45] Date of Patent: Jan. 28, 1992

[54] PROCESS FOR PRODUCING 1,3-SUBSTITUTED TETRAHYDRO-1H-THIENO-[3,4-D]-IMIDAZOL-2(3H)-ON-4-YLIDENE PENTANOIC ACID ESTER

[75] Inventor: Martin Eyer, Glis, Switzerland

[73] Assignee: Lonza Ltd., Gampel/Valais, Switzerland

[21] Appl. No.: 491,589

[22] Filed: Mar. 12, 1990

[30] Foreign Application Priority Data

Mar. 15, 1989 [CH] Switzerland ............................ 953/89

[51] Int. Cl.$^5$ .............................................. C07F 9/54
[52] U.S. Cl. ...................................... 548/113; 548/303
[58] Field of Search ................................ 548/303, 113

[56] References Cited

U.S. PATENT DOCUMENTS

| | | | |
|---|---|---|---|
| 2,489,232 | 11/1949 | Goldberg et al. | 260/368 |
| 2,489,235 | 11/1949 | Goldberg et al. | 260/309 |
| 2,535,010 | 12/1950 | Croxall | 260/184 |
| 2,784,191 | 3/1957 | Fischer et al. | 260/294.7 |
| 4,054,740 | 10/1977 | Field | 548/303 |
| 4,118,396 | 10/1978 | Pifferi et al. | 260/326.43 |
| 4,124,594 | 11/1978 | Monguzzi et al. | 260/326.43 |
| 4,173,569 | 11/1979 | Banfi et al. | 260/326.43 |

FOREIGN PATENT DOCUMENTS

| | | | |
|---|---|---|---|
| 161580 | 11/1985 | European Pat. Off. | |
| 173185 | 8/1986 | European Pat. Off. | |
| 192255 | 8/1986 | European Pat. Off. | |
| 273270 | 12/1987 | European Pat. Off. | 548/303 |
| 850007 | 7/1952 | Fed. Rep. of Germany | |
| 2058248 | of 1970 | Fed. Rep. of Germany | |
| 2058234 | 6/1971 | Fed. Rep. of Germany | |
| 37775 | 11/1970 | Japan | |
| 37776 | 11/1970 | Japan | |
| 46-3580 | 1/1971 | Japan | |
| 53-15074 | 1/1978 | Japan | |
| 183756 | 11/1982 | Japan | |

OTHER PUBLICATIONS

C.A., vol. 52, Para 11124g.
C.A., vol. 74, Para 100018h.
C.A., vol. 105, Para 226341.
Cram et al., J. Am. Chem. Soc. 1963, 85, pp. 1430–1437.
Ho et al., "Cleavage of Esters and Ethers with Iodotrimethyl Silane", Angewandte Chemie, vol. 15, No. 12, (Dec. '76), pp. 774–775.
Kochler, Dissertation Bayreuth (1985).
Lowe, G. et al, J. Chem. Soc., Perkins Trans. I 1973), pp. 2907–2910.
Mackenzie et al., J.O.C.S., 20, No. 12 (1955), pp. 1695–1696. .
G. Pifferi et al., Il Farmaco, Ed. Sc. (1977), 32, pp. 602–613.
Sidgwick, "The Organic Chemistry of Nitrogen", 3rd Ed, Oxford (1966), p. 637.
Tanaka et al., Chem. Pharm. Bull., vol. 32, No. 8, pp. 3291–3298.
English–Language Abstract of German OS 850007.
D. A. Clark et al., Synthesis, (1977), pp. 628 and 629.

*Primary Examiner*—Robert Gerstl
*Attorney, Agent, or Firm*—Fisher, Christen & Sabol

[57] ABSTRACT

Process for the preparation of 1,3-substituted tetrahydro-1H-thieno[3,4-d]-imidazol-2(3H)-on-4-ylidene pentanoic acid esters which are intermediate products for the production of the pharmaceutic active substance (+)-biotin.

2 Claims, No Drawings

5,084,578

PROCESS FOR PRODUCING 1,3-SUBSTITUTED TETRAHYDRO-1H-THIENO-[3,4-D]-IMIDAZOL-2(3H)-ON-4-YLIDENE PENTANOIC ACID ESTER

BACKGROUND OF THE INVENTION

1. Field Of The Invention

The invention relates to a process for producing 1,3-substituted tetrahydro-1H-thieno-[3,4-d]-imidazol-2(3H)-on-4-ylidene pentanoic acid ester as suitable precursors for producing (+)-biotin.

2. Background Art (+)-Biotin is known as a human vitamin, vitamin H. But biotin is also used as a pharmaceutical active substance for the treatment of dermatosis and as a feed additive with growth enhancing effect for working animals.

From European Published Patent Application No. 273,270 it is known that, in an intermediate stage in the synthesis of (+)-biotin, 1,3-substituted tetrahydro-1H-thieno-[3,4-d]imidazol-2(3H)-on-4-ylidene pentanoic acid ester is produced from 1,3-substituted tetrahydro-1H-thieno-[3,4-d]-imidazol-2,4-dione by a Grignard reaction or by a Wittig reaction. However, the very poor yields of 12 percent with the Wittig reaction or 28 percent with the Grignard reaction are a serious disadvantage.

Broad Description Of The Invention

The object of the invention is to significantly improve this stage in the synthesis of biotin with respect to the yield.

The object of the invention is achieved by the process of the invention.

The invention involves a process for the preparation of 1,3-substituted tetrahydro-1H-thieno-[3,4-d]-imidazol-2(3H)-on-4-ylidene pentanoic acid ester. The invention process includes reducing a 1,3-substituted tetrahydro-1H-thieno-[3,4-d]-imidazol-2,4-dione of the formula:

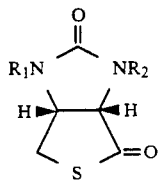

II wherein $R_1$ is an (R)- or (S)-phenylalkyl group, an (R) or (S)-1-alkoxycarbonyl-1-phenylmethyl group or an (R) or (S)-1-aryloxycarbonyl-1- phenylmethyl group and $R_2$ is hydrogen, a substituted or unsubstituted alkanoyl group, a unsubstituted or substituted benzoyl group, a benzyl group, an alkoxycarbonyl group, an aryloxycarbonyl group, an aryloxyalkyl group, an alkoxyalkyl group, a pyranyl group, a unsubstituted or substituted benzenesulfonyl group, an alkylsulfonyl group, a diarylphosphinyl group, a dialkoxyphosphinyl group or a trialkylsilyl group, with a reducing agent to the corresponding hydroxy compound. The corresponding hydroxy compound is reacted with a phosphonium salt of the formula:

III wherein $R_3$ is an alkyl group with 1 to 20 C atoms, an aryl or benzyl group and X is a halogen atom, $BF_4^-$, $ClO_4^-$, $I_3^-$ or $PF_6^-$, to provide a phosphonium compound of the formula:

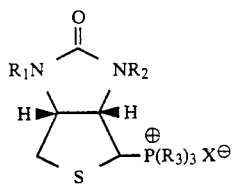

IV wherein $R_1$, $R_2$, $R_3$ and X have the above-mentioned meanings. The phosphonium compound is reacted in the presence of a strong base with a 5-oxo-valeric acid ester of the formula:

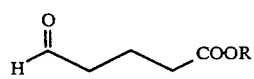

V wherein R is a $C_1$–$C_6$ alkyl group which is a straight-chain or branched and which is substituted or unsubstituted, or a phenyl or benzyl group which is unsubstituted or substituted with at least one halogen atom or alkyl or aryl group, into the 1,3-substituted tetrahydro-1H-thieno-[3,4-d]-imidazol-2(3H)-on-4-ylidene pentanoic acid ester of the formula:

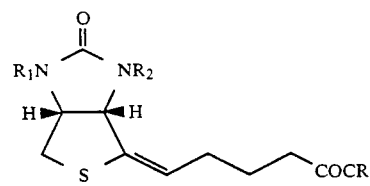

I wherein R, $R_1$ and $R_2$ have the above-mentioned meaning.

Suitably R is a methyl, ethyl, propyl, i-propyl, butyl, phenyl or a benzyl group. Suitably $R_1$ is a (R)- or (S)-1-phenylalkyl group, preferably an (R)- or (S)-1-phenylethyl group, $R_2$ preferably is hydrogen or a benzyl, acetyl, tertbutoxycarbonyl, 4-methoxybenzyl or methoxymethyl group. $R_3$ suitable is ($C_1$-$C_4$) alkyl, benzyl and phenyl, particularly phenyl.

The production of the 1,3-substituted tetrahydro-1H-thieno-[3,4-d]-imidazole-2,4-diones, which are the starting compounds in the invention process, is known from European Published Patent Application No. 273,270.

For the reduction of the 1,3-substituted tetrahydro-1H-thieno-[3,4-d]-imidazole-2,4-diones of formula II, diisobutylaluminum hydride, sodium borohydride, botane complexes or complex aluminum hydrides are suitably used. Preferably diisobutylaluminum hydride is used at a temperature between −80° and 25° C. The reducing agent is suitably added in an excess of 5 to 20 percent, in relation to the starting compound. The reduction takes place advantageously in the presence of an inert solvent, such as, toluene, tetrahydrofuran, ether, benzene or dimethoxyethane. After a reaction time of usually 15 to 120 minutes, the resulting 1,3-substituted 4 hydroxy-1H-thieno-[3,4-d]-imidazol-2(3H)-one can be isolated in a conventional or usual manner. The yield in this first stage is almost quantitative, as a rule.

The next stage comprises the formation of the phosphonium compound of the formula:

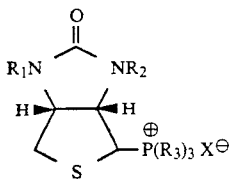

with the help of a phosphonium salt of the formula:

$(R_3)_3PH^{\oplus}X^{\ominus}$  III wherein the substituents $R_3$ and X have the above-mentioned meaning.

The phosphonium compounds of formula IV have not been previously described. As new intermediate products they are an essential component of the invention process.

Particularly suitable phosphonium salts of formula III are triphenyl phosphoniumtetrafluoroborate or triphenylphosphonium chloride. The phosphonium salts of formula III as a rule are produced shortly before their use in a known manner, e.g., according to D. A. Clark et al., Synthesis, (1977), 628.

The reaction providing the phosphonium compounds of formula IV takes place, depending on the solvent, suitably at a temperature of −20° to 100° C., advantageously at 60 to 80° C., in an inert solvent. Suitable inert solvents are, for example, acetonitrile, tetrahydrofuran, ether, dioxane or dimethoxyethane, and preferably acetonitrile. After a reaction time of 30 to 300 minutes, the phosphonium compound of formula IV can be isolated and optionally purified in almost quantitative yield in a manner conventional or known in the art.

The last stage in the invention process comprises the conversion of the phosphonium compound of formula IV in the presence of a strong base with a 5-oxo valeric acid ester of formula V into the end product. As the strong base, alkali alcoholates of alcohols with one to four C atoms, e.g. potassium tert-butylate or sodium methylate, or an alkyl lithium, e.g., n-butyl lithium, or an alkali hexamethyldisilazide, e.g., sodium hexamethyldisilazide, or an alkali hydride, e.g., sodium hydride, can be used. Particularly suitable is potassium tert-butylate or sodium hexamethyldisilazide. Suitably the base is used in an excess of 5 to 20 percent, preferably of 10 to 15 percent. The reaction temperature is advantageously kept between −20° and 60° C., quite suitably between 0° and 25° C. Further, it is useful to conduct the reaction in the presence of an inert solvent, such as, tetrahydrofuran, dimethylsulfoxide or ether. After a reaction time of 2 to 24 hours the end product can be isolated and optionally purified in a conventional or usual manner from the reaction mixture in yields of up to 70 percent.

Thus, with the three stage process according to the invention an overall yield of over 60 percent can be achieved.

Detailed Description Of The Invention

The Example (a) Production of (3aS,6aR)-3-benzyl-1-[(R)-(1-phenylethyl)]tetrahydro-4-hydroxy-1H-thieno-3,4-d1-imidazol-2(3H)-one 10 ml of a 1.2 M solution of diisobutylaluminum hydride in toluene was slowly instilled into a solution, cooled to −70° C., of 3.52 g (10 mmol) of (3aS,6aR)-3-benzyl-1-[(R)-(1-phenylethyl)]-tetrahydro-1H-thieno-[3,4-d]-imidazole-2,4-dione in 120 ml of toluene with stirring, and the temperature of the reaction solution did not rise above −60°. After the addition was ended, it was stirred for 2 hours at −70° C. and 50 ml of 10 percent aqueous ammonium chloride solution as added. The partly precipitated white product was filtered off, the phases were separated and the aqueous phase was extracted twice more with ethyl acetate. The combined organic phases were dried with MgSO$_4$ and concentrated by evaporation on the rotavapor. The white residue was combined with the product already filtered off. In total, 3.49 g (98.6 percent) of (3aS,6aR)-3-benzyl-1-[(R)-(phenylethyl)]-tetrahydro-4-hydroxy-1H-thieno[3,4-d]-imidazol-2(3H)-one was obtained as a (94:6) diastereomeric mixture. The following spectroscopic data are from the main diastereoisomer (mp 216°–217° C.):

IR (KBr) 3235, 2930, 1668, 1470, 1245, 1040, 754

$^1$H-NMR (d$_6$DMSO) 1.58 (d,J=7.5 Hz, 3H) 2.25 (d,J=12.5 Hz, 1H) 2.85 (dd,J=5 Hz, 12.5 Hz, 1H) 3.90 (d,J=8.7 Hz, 1H) 4.25 (d,J=15 Hz, 1H) 4.55 (m, 1H) 4.60 (d,J=15 Hz, 1H) 5.05 (q,J=7.5 Hz, 1H) 5.22 (d,J=4.5 Hz, 1H) 6.00 (d,J=4.5 Hz, 1H) 7.20–7.50 (m, 10H)

MS (m/e) 354 (M$^+$,2) 187 (28), 105 (66), 97 (16), 91 (100), 77 (14), 44 (19), 36 (38)

(b) Production of (3aS,6aR)-3-benzyl-1-(R)-1(1-phenylethyl)1-tetrahydro-4-triphenyl phosphonium-1H-thieno-[3,4-d1-imidazol-2(3H)-one-tetrafluoroborate A solution of 0.70 g (2 mmol) of (3aS,6aR)-3-benzyl-1-[(R)-1(1-phenylethyl)]-tetrahydro-4-triphenyl phosphonium-1H-thieno-[3,4-d]-imidazol-2(3H)-one and 0.77 g (2.2 mmol) of triphenylphosphonium tetrafluoroborate in 20 ml of acetonitrile was refluxed for 2 hours. Checking by TLC showed that no more educt was present. The solvent was distilled off on the rotavapor and the residue was dried. The yield was 1.35 g (98.5 percent) of (3aS,6aR)-3-benzyl-1-[(R)-1(1-phenylethyl)]-tetrahydro-4-triphenyl phosphonio-1H-thieno-[3,4-d]-imidazol-2(3H)-one-tetrafluoroborate, which had a melting point of 116° to 118° C. The spectroscopic data was:

IR (Kbr) 2935, 1697, 1479, 1450, 1439, 1427, 1252, 1107, 1071, 1036, 996, 738, 689

$^1$H-NMR (CDCl$_3$) 1.15 (dd, J=5.0 Hz, 12.5 Hz, 1H) 1.55 (d,J=7.5 Hz, 3H) 1.85 (d,J=12.5 Hz, 1H) 4.28 (d,J=17.5 Hz, 1H) 4.40–4.50 (m, 1H) 4.80–4.90 (m, 1H) 4.90 (d,J=17.5 Hz, 1H) 5.05 (t,J=7.5 Hz, 1H) 5.28 (q,J=7.5 Hz, 1H) 7.15–7.50 (m, 15H) 7.55–7.85 (m, 10H)

(c1) Production of (3aS,6aR)-3-benzyl-1-(R)-(1-phenylethyl)1-tetrahydro-1H-thieno-[3,4-d1-imidazol-2(3H)-on-4-ylidene pentanoic acid methylester In portions 0.44 g (3.80 mmol) of freshly sublimated potassium tert-butylate was added to a solution of 2.28 g (3.30 mmol) of (3aS,6aR)-3-benzyl-1-[(R)-(1-phenylethyl)]-tetrahydro-4-triphenyl phosphonio-1H-thieno-[3,4-d]-imidazol-2(3H)-one-tetrafluoroborate in 30 ml of tetrahydrofuran at room temperature. The orange red reaction mixture was stirred for 2 hours at room temperature and then 0.53 g (3.80 mmol) of 5-oxo-valeric acid methylester, diluted with 1 ml of tetrahydrofuran, was slowly instilled. The reaction mixture was stirred overnight, taken up in water/ethyl acetate and the solvent was concentrated by evaporation on the rotavapor. Silica gel chromatography with ethyl acetate/hexane as the eluant yielded 0.97 g (65 percent) of (3aS,-6aR)-3-benzyl-1-[(R)-(1-phenylethyl)]-tetrahydro-1H-thieno-[3,4-d]-imidazol-2(3H)-on-4-ylidene pentanoic acid methyl ester as a colorless oil. The spectroscopic data was:

IR (Film) 2935, 1736, 1694, 1435, 1415, 1360, 1245, 1216, 1168, 756, 702

$^1$H-NMR (CDCl$_3$) 1.45–1.60 (M, 2H) 1.68 (d,J=7.5 Hz, 3H) 1.75–1.88 (m, 2H) 2.08 (t,J=7.5 Hz, 2H) 2.28 (dd,J=3 Hz, 12.5 Hz, 1H) 2.52 (dd,J=5.5 Hz, 12.5 Hz, 1H) 3.60 (s, 3H) 4.02 (d,J=16.0 Hz, 1H) 4.33–4.41 (m, 1H) 4.65 (d,J=7.5 Hz, 1H) 4.92 (d,J=16.0 Hz, 1H) 5.38 (q,J=7.5 Hz, 1H) 5.60 (t,J=7.5 Hz, 1H) 7.15–7.50 (m, 10H)

MS (m/e) 450 (M+,1H) 345 (5), 237 (14), 120 (20), 105 (80), 91 (100), 79 (14), 44 (10)

(c2) production of (3aS,6aR)-3-benzyl-1-(R)-(1-phenylethyl)1-tetrahydro-1H-thieno-[3,4-d]-imidazol-2(3H)-on-4-ylidenepentanoic acid hexylester In portions 0.47 g (4.19 mmol) of freshly sublimated potassium tert-butylate was added to a solution of 2.60 g (3.64 mmol) of (3aS,6aR)-3-benzyl-1-[(R)-1(1-phenylethyl)]tetrahydro-4-triphenyl phosphonio-1H-thieno-[3,4-d]-imidazol-2(3H)-one-tetrafluoroborate in 35 ml of tetrahydrofuran at room temperature. The orange red mixture was stirred for 2 hours at room temperature and then 0.84 g (4.20 mmol) of 5-oxo-valeric acid hexylester, diluted with 1 ml of tetrahydrofuran, was slowly instilled. The reaction mixture was stirred overnight, taken up in water/ethyl/acetate and the solvent was removed on the rotavapor. Silica gel chromatography with ethyl acetate/hexane as the eluent yielded 1.10 g (58 percent) of (3aS,6aR)-3-benzyl-1-[(R)-(1-phenylethyl)]-tetrahydro-1H-thieno-[3,4-d]-imidazol-2(3H)-on-4-ylidene pentanoic acid hexylester as a faintly yellowish oil. The spectroscopic data was:

IR (Film) 2931, 1732, 1696, 1432, 1413, 1359, 1244, 1216, 1169, 756, 701

$^1$H-NMR (CDCl$_3$) 0.85–1.00 (m, 3H) 1.25–1.45 (m, 6H) 1.55–1.80 (m, 7H) 1.95–2.15 (m, 2H) 2.27 (t,J=7.5 Hz, 2H) 2.38 (dd, J=3 Hz, 12.5 Hz, 1H) 2.49 (dd,J=5.5 Hz, 12.5 Hz, 1H) 4.00–4.10 (m, 3H) 4.20–4.30 (m, 2H) 4.93 (d,J=15.5 Hz, 1H) 5.32–5.45 (m, 2H) 7.20–7.50 (m, 10H)

MS (m/e) 520 (M+,15), 487 (10), 415 (32), 253 (14), 237 (41), 187 (11), 132 (17), 120 (21), 105 (100), 91 (92), 43 (28)

(c3) production of (3aS,6aR)-3-benzyl-1-[(R)-(1-phenylethyl)1-tetrahydro-1H-thieno-[3,4-d]-imidazol-2(3H)-on-4-ylidenepentanoic acid benzylester In portions of 0.54 g (4.78 mmol) of freshly sublimated potassium tert-butylate was added to a solution of 2.85 g (4.15 mmol) of (3aS,6aR)-3-benzyl-1-[(R)-1(1-phenylethyl)]tetrahydro-4-triphenyl phosphonio-1H-thieno-[3,4-d]-imidazol-2(3H)-one-tetrafluoroborate in 35 ml of tetrahydrofuran at room temperature. The orange red mixture was stirred for 2 hours at room temperature and then 0.99 g (4.78 mmol) of 5-oxo-valeric acid benzylester, diluted with 1 ml of tetrahydrofuran, was slowly instilled. The reaction mixture was stirred overnight, taken up in water/ethyl/acetate and the solvent was concentrated by evaporation on the rotavapor. Silica gel chromatography with ethyl acetate/hexane as the eluent yielded 1.57 g (72 percent) of (3aS,6aR)-3-benzyl-1-[(R)-(1-phenylethyl)]-tetrahydro-1H-thieno-[3,4-d]-imidazol-2(3H)-on-4-ylidene pentanoic acid benzylester as a colorless oil. The spectroscopic data was:

IR (Film) 2935, 1734, 1694, 1444, 1414, 1358, 1236, 1215, 1161, 752, 700

$^1$H-NMR (CDCl$_3$) 1.62–1.78 (m, 5H) 1.98–2.15 (m, 2H) 2.33 (t,J=7.5 Hz, 2H) 2.38 (dd,J=4 Hz, 12.5 Hz, 1H) 2.46 (dd,J=5.5 Hz, 12.5 Hz, 1H) 4.03 (d,J=15.5 Hz, 1H) 4.18–4.28 (m, 2H) 4.93 (d,J=15.5 Hz, 1H) 5.11 (s, 2H) 5.33–5.42 (m, 2H) 7.20–7.50 (m, 15H)

MS (m/e) 526 (M+,14), 493 (10), 435 (12), 421 (20), 331 (10), 253 (10), 237 (31), 187 (17), 132 (10), 105 (65), 91 (100), 79 (8), 65 (4)

What is claimed:

1. A phosphonium compound of the formula:

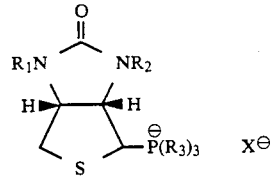

wherein R$_1$ is (R)- or (S)-1-phenylalkyl group, or an (R)- or (S)-1-alkoxycarbonyl-1-phenylmethyl group, R$_2$ is hydrogen, an alkanoyl group, a benzoyl group, a benzyl group, an alkoxycarbonyl group, an alkoxy alkyl group, a pyranyl group, a benzenesulfonyl group, an alkylsulfonyl group, a dialkoxyphosphinyl group or a trialkylsilyl group, R$_3$ is an alkyl group with 1 to 20 C atoms, a phenyl group or a benzyl group, and X is a halogen atom, BF$_4^-$, ClO$_4^-$, or PF$_6^-$.

2. The phosphonium compound according to claim 1 wherein said phosphonium compound is (3aS,6aR)-3-benzyl-1-[(R)-1(1-phenylethyl)]-tetrahydro-4-triphenylphosphonium-1H-thieno-[3,4-d]-imidazol-2(3H)-onetetrafluoroborate.

* * * * *